United States Patent
Zhang

(10) Patent No.: US 6,938,574 B2
(45) Date of Patent: Sep. 6, 2005

(54) REARING FLY LARVAE AND ANIMALS IN SPACE FOR WASTE RECYCLING AND FOOD SUPPLYING

(76) Inventor: Mao Zhang, 5578 Spur Ct., Fontana, CA (US) 92336

( * ) Notice: Subject to any disclaimer, the term of this patent is extended or adjusted under 35 U.S.C. 154(b) by 0 days.

(21) Appl. No.: 10/619,130

(22) Filed: Jul. 15, 2003

(65) Prior Publication Data

US 2004/0089241 A1 May 13, 2004

Related U.S. Application Data

(63) Continuation-in-part of application No. 10/178,344, filed on Jun. 25, 2002.

(51) Int. Cl.$^7$ ............................................. A01K 29/00
(52) U.S. Cl. ..................................... 119/6.6; 119/6.5
(58) Field of Search ................... 119/6.6, 6.5

(56) References Cited

U.S. PATENT DOCUMENTS

| | | | | |
|---|---|---|---|---|
| 3,814,057 A | * | 6/1974 | Calvert et al. | 119/6.6 |
| 4,023,954 A | * | 5/1977 | de Maudave | 71/15 |
| 5,618,574 A | * | 4/1997 | Bunch | 426/641 |
| 5,985,538 A | * | 11/1999 | Stachecki | 435/1.1 |
| 6,130,084 A | * | 10/2000 | Endencia et al. | 435/305.1 |
| 6,303,175 B1 | * | 10/2001 | Kurzinger et al. | 426/573 |
| 6,557,487 B1 | * | 5/2003 | Fleischmann | 119/6.5 |

FOREIGN PATENT DOCUMENTS

| | | | | | |
|---|---|---|---|---|---|
| GB | 2110516 A | * | 11/1982 | | A01K/29/00 |
| JP | 59085259 A | * | 11/1982 | | A23K/1/18 |
| JP | 62269646 A | * | 5/1986 | | A23K/1/00 |
| JP | 06116073 A | * | 10/1992 | | A01G/7/00 |
| JP | 6116073 | | 4/1994 | | |
| WO | WO 74478 A1 | * | 12/2000 | | A01K/67/033 |

OTHER PUBLICATIONS

New Scientist, Feedback, vol. 141, No. 1981, p. 92, Mar. 26, 1994.*

Mini–livestock, village development and role of BEDIM; Hardouin,; Universitaire des Sciences Agronomiques de Gembloux, Passage des Deportes, B–5030 Gembloux, Belgium, BASE: Biotechnologie, Agronomie, Societe et Environemnt coil. 1 (2):p.9 99 abstract 1p.*

* cited by examiner

*Primary Examiner*—Peter M. Poon
*Assistant Examiner*—Andrea M. Valenti

(57) ABSTRACT

In space, wastes from humans, animals, and crops can be fully recycled by rearing maggots which will be nourishing feedstuff for feeding animals. These animals and their eggs combined with crop plants will be varied food for humans in space. Water and nutrition left in the residues remaining after rearing the maggots can be recycled and used to fertilize crop plants. Rearing maggots, animals, and crop plants provides a self-sufficient food regenerative system that enables humans to live and work in space on long term missions independent of food from earth.

4 Claims, No Drawings

REARING FLY LARVAE AND ANIMALS IN SPACE FOR WASTE RECYCLING AND FOOD SUPPLYING

This application is a continuation-in-part of application Ser. No. 10/178,344, filed on Jun. 25, 2002.

BACKGROUND OF THE INVENTION (1) Field of the Invention

A method of waste recycling for food regeneration in the space.

(2) Background Art

Scientists in many countries such as China, the USSR, the United States, Mexico, Eastern Europe, Israel, Australia and South America have studied rearing maggots in manure to convert residual protein and other nutrients in animal manures to high quality maggot biomass for use as animal feedstuff.

In U.S. Pat. No. 5,618,574, Bunch discloses using dried fly larvae as fish food to improve the growth, feeding efficiency and coloration of fish.

BRIEF SUMMARY OF THE INVENTION

In this invention we propose rearing one type of maggot—housefly larvae (HFL) as a space food source in addition to crop plants for waste recycling and food production in long term mission. Housefly larvae have great vitality and seldom get disease. They can be easily reared in a small volume of containers where housefly larvae and feedstuff could closely touch in microgravity under controlled constant temperature and humidity condition without much care. The feedstuff is made by mixing human/animal wastes (feces, urine; animal dejecta and leftover bits) and cast-off crops (such as wheat bran and bean dregs). The crops may also be cultivated as space food by NASA.

Thus the feedstuff nutrition from both human/animals wastes and crop waste can be all recycled to achieve the goal of efficiently producing nourishing housefly larvae. The housefly larvae will be the food source for feeding animals.

The water and nutrition left in the residues remaining after rearing housefly larvae can be recycled and used to fertilize crop plants. Current self-supported space foods—the crop plants such as wheat, potato, and beans—mainly offer calories and the plant proteins needed by the human body. They cannot offer other nutrients such as animal protein, fatty acids, amino acids and so on. The housefly larvae body consists of rich protein, 18 kinds of amino acids (10 kinds are necessary for the human body), fatty acids and many kinds of vitamins, minerals, and electrolytes. Live housefly larvae and housefly larvae power will be the ideal feedstuff for animals, such as poultry, aquatic animals, amphibians, and livestock. These animal bodies combined with their eggs will provide a varied ideal food—they are all meat diets for humans in space. Fly eggs have very strong reproduction and growth abilities.

Their reproduction and growth cycles are very short. They usually mature in 4 days after being hatched, and their weight increase by 250~300 times. Frozen maggot eggs have a long life and keep their reproduction ability. For 5 crew in a ten year mission, around 25 kg of fly eggs could be brought from earth at the beginning to provide a food source without need for subsequent deliveries. Rearing maggots and animals combined with crop plants in space would be a regenerative integrated system with closed loops of food, water, and air recovery from most wastes. The operations involved in rearing maggots meet restrictions related to volume, mass, energy and labor. It is an efficient, reliable and effective bioregenerative system for long term missions.

DETAILED DESCRIPTION OF THE INVENTION

To date, all crewed space missions have been short-term and in low earth orbit. They have relied on food replenishment from earth. Wastes must be discarded or stored until the crew return to earth. But for future long-term missions and permanent planetary bases such as those on the moon and Mars, it will not be possible to supply the crew from earth. The recovery and recycling of nutrients from wastes to support food production must be performed in space, however, current technology cannot support this goal. For example, NASA's crop-plant-based bioregenerative systems satisfy only a fraction of the total waste recycling (mainly $CO_2$ and gray water) and food requirements. These systems also require high levels of light energy for maximum photosynthesis, large growing areas, and long growing periods. So current NASA Advanced Life Support technology cannot provide the life support functions needed for long term human exploration of space in a cost-effective manner.

Here we propose rearing one type of maggot—housefly larvae—as a space food source to use in addition to crop plants for waste recycling and food production on long term missions. As we know, maggots readily feed on fresh manure and convert residual protein and other nutrients into biomass, which is a high quality animal feedstuff with rich protein and other nutrients. The fly eggs can be provided with minimum effort on long term missions by freezing them in liquid nitrogen, so they can be hatched and reared by warming them at any time. Maggots are fly larvae (FL), the scientific name of the housefly (HF) is *Musca Domestica*. We select Housefly Larvae (HFL) as a first candidate in our invention, because, HFL have strong reproduction ability, short life cycle, seldom get diseases, and are easily reared in high densities with high efficiency and without much care. It is well known from many studies that HFL have the ability to flourish in virtually any animal manure (and certainly human manure too). They can convert these wastes to high quality nourishing animal feedstuff without poison. The equipment and techniques needed to raise them are simple. Also, feeding, processing, and storage of HFL, and the use of HFL as feedstuff for various animals are all mature technique on the ground. It may therefore be easier to transfer these techniques to space usage with less time and investment.

We do not select HF pupae as our first candidate even though pupae contain rich nutrition and are easy to harvest. The reason is that there is a loss of biomass in pupal development. Pupae are about half weight of mature maggots and the larger amount of chitinous exoskeleton in the adult may reduce nutrient availability.

Housefly larvae have a fabulous reproduction speed. A couple of housefly larvae can produce around 1000 eggs during their reproduction period (12-15 days). Theoretically, 1000 eggs can reproduce 200 billion adult HFL within four months. 200 billion HFL contain more than 600 tons of pure protein. The egg usually take 4 days to become mature HFL and 10 days to fly. They have a short and speedy reproduction period and a high output. The weight of one HF egg is around 0.08 mg (one gram of HF eggs contains 12000–14000 eggs), the weight of one adult maggot will be 20~30 mg, which is 250~350 times larger after being reared for 4 days. To date, housefly larvae are second-to-none in producing animal protein. Moreover, rearing HFL in the darkness in an aeration room with temperatures of 25–28° C. and comparative humidity 60–80%, allows them to reproduce continuously generation after generation. HFL are light avoiding insects, so they should be reared in dark containers instead of in the light as for plant photosynthesis.

Nutritional Content of Housefly Larvae

The data below is from four national academic institutes in China (See, Wang Darui et al, Entomologica. Knowledge 1991 (4): 247–249 "Analysis and utilizing of the Nutritional Contains of Housefly Larvae."; Zhang Zhe sheng, et al, Science and Technology of Food Industry 1997 (6): 67–69 "Exploration House Fly Larvae as a Potential Food Protein Resource for Human."; Li Guanghong, et al, Entomological Knowledge, 1997 34 (6): 347–349; "Nutritional evaluation or extracted Housefly Protein."; and Wei Yongping et al, China Agriculture Press, Beijing, August 2001, "Raising of Economic Insects and Its Exploitation.")

The Analysis of Housefly Larvae Nutrition

Housefly larvae powder is dried from fresh HFL. Its weight is about ⅓ that of fresh HFL. HFL powder contains 54–63% protein which is more than that of fishmeal powder. Fat accounts for 11–17% of HFL powder, similar to plant oil or fish liver oil. Amino acids are well combined with 9 kinds of essential amino acids for humans. The total amount of essential amino acids crucial to human life is 2.3 times that of fishmeal, storage of lysine, methionine and phenylalanine is 2.6, 2.7, and 2.9 times that of fishmeal, respectively. Two of the essential amino acids, lysine and tryptophan, are poorly represented in most plant proteins. The essential amino acids account for 43–47% (E %), which is more than the referenced standard (40%) issued by FAO/WHO. Essential amino acids/non-essential (E/N) is 0.70–0.89, which is much more than the referenced standard (60%) issued by FAO/WHO.

HFL powder contains rich amounts of K, Na, Ca, Mg, P and many trace elements necessary for humans such as Zn, Fe, Mn, Cu, B, P, Gr, Co, Al, Si, etc, and also contains sufficient vitamin A, D and B. The content of vitamin D is similar to that of fish-liver. Notably, HFL powder contains rich amounts of vitamins $B_1$ and $B_{12}$ that are insufficient in crops. $B_1$ and $B_2$ levels are, respectively, 15 and 1800 times those of milk.

TABLE 1

Nutritional content of HFL powder, HFL protein powder and fishmeal (%)

| Content | HFL powder | | | HFL protein powder | Fishmeal |
|---|---|---|---|---|---|
| Protein | 60.88 | 54.47 | 62.70 | 73.03 | 38.6–61.6 |
| Carbohydrate | | 12.04 | | 0 | 2.80 |
| Fat | 17.1 | 11.60 | 11.20 | 23.10 | 1.2 |
| Gross Fiber | | 5.70 | | 0 | 19.41 |
| Ash Content | 9.2 | 11.43 | 10.42 | 1.83 | 20 |
| Moisture Content | | 5.80 | 5.10 | 3.34 | 11.40–13.50 |
| Chitin | | | 3.97 | | |

HFL protein powder is enriched from HFL powder processed using acid deposition techniques.

TABLE 2

HFL Fatty acid Contains of Fatty acid (g/100 g)

| Myristic acid | 2.2 | Linoleic acid | 32.5 |
|---|---|---|---|
| Palmitic acid | 19.7 | Linolenic acid | 3.3 |
| Stearic acid | 2.3 | Saturated fatty acid | 27.4 |
| Palmitoleic acid | 12.7 | Unsaturated fatty acid | 68.2 |
| Oleic acid | 18.2 | Essential fatty acid | 36.0 |

Table 2 shows how non-saturated fatty acids in HFL powder account for 68.2% of total amount of fatty acids.

Essential fatty acids account for 36% (Mainly Linoicic acid). Plant oil contains much more Linoleic and Linolenic acid with richer nutrition than those of animals. HFL belong to animality, but contains much more essential fatty acid than peanut oil or vegetable seed oil.

TABLE 3

Amino Acids of HFL powder, HFL Protein powder and fishmeal (%)

| Amino Acid | HFL | | | HFL protein | | Fishmeal |
|---|---|---|---|---|---|---|
| Aspartic acid | | 5.4 | 6.18 | 9.58 | 7.60 | 2.85 |
| Threonine* | 2.30 | 2.39 | 2.03 | 4.59 | 3.17 | 1.15 |
| Serine | | 1.83 | 1.58 | 4.03 | 2.57 | 1.34 |
| Glutamic acid | | 8.91 | 8.20 | 15.06 | 10.67 | 5.34 |
| Glycine | | 2.36 | 3.84 | 4.55 | 2.67 | 3.27 |
| Alanine | | 3.64 | 2.49 | 6.10 | 3.21 | 2.28 |
| Cystine* | 0.43 | 0.31 | 0.67 | 1.17 | 0.50 | 0.23 |
| Valine* | 2.76 | 2.87 | 3.23 | 5.05 | 3.71 | 1.58 |
| Methionine* | 1.49 | 1.26 | 1.25 | 2.42 | 2.27 | 0.46 |
| Isoleucine* | 2.34 | 3.10 | 2.54 | 4.21 | 3.98 | 1.09 |
| Leucine* | 3.57 | 3.85 | 4.05 | 6.92 | 5.68 | 2.07 |
| Tyrosine | 4.30 | 3.24 | 3.22 | 6.15 | 5.27 | 1.37 |
| Phenylalanine* | 4.32 | 3.08 | 3.51 | 5.74 | 4.87 | 1.19 |
| Lysine* | 4.30 | 4.45 | 4.30 | 9.32 | 4.97 | 1.64 |
| Arginine | | 2.18 | 3.70 | 5.23 | 3.88 | 2.31 |
| Histidine | | 1.27 | 1.96 | 2.91 | 1.59 | 0.70 |
| Proline | | 2.19 | 4.16 | 4.08 | 2.34 | 2.79 |
| Tryptophan* | 0.78 | | | 1.10 | | |
| E | 27.59 | 24.65 | 24.80 | 46.67 | 34.42 | 10.78 |
| N | 27.68 | 32.47 | | 51.54 | 34.62 | 21.29 |
| E + N | | 52.33 | 57.27 | 98.21 | 69.04 | 32.07 |
| E % | | 47 | 43 | 48 | 49 | 34 |
| E/N | | 0.89 | 0.76 | 0.90 | 0.99 | 0.50 |

(*Amino Acids essential for human)
E: Total amount of essential amino acid,
N: Total amount of non-essential amino acid.
E %: Percentage of essential amino acid,
E/N: Ratio of essential amino acid and non-essential amino acid.

TABLE 4

Analysis Result of Several Minerals and Trace Elements in HFL Powder Minerals and elements (PPM)

| K | 71.72 | Zn | 4.40 |
|---|---|---|---|
| Na | 20.00 | Fe | 2.33 |
| Mg | 26.97 | Mn | 1.98 |
| Ca | 34.12 | Cu | 0.29 |
| P | 62.35 | B | 0.19 |

TABLE 5

Analysis Result of Vitamin Content in HFLs Contains of Vitamin (mg/100 g)

| K | 0.35 | B1 | 12.85 |
|---|---|---|---|
| A | 1.17 | B2 | 28.86 |
| D | 1.08 | B6 | 7.83 |
| E | 0.45 | B12 | 188.04 |

Storage of HF Eggs and HFL Food in Space:

1. Cryopreservation of Fly Eggs in Long Duration Missions.

Our invention provides nutritional food for the crew of a spaceship by rearing HFL and feeding animals in space.

We propose to only rear HFL instead of flies in space, because rearing flies in space would take more room and labor than rearing larvae, There is a need to bring adequate fly eggs from earth for food source storage in long term missions. Fly eggs could become HFL after being hatched. HFL mature in 4 days and could become animal feedstuff by producing HFL or HFL powder.

Frozen HF eggs stored for long term missions may maintain their strong reproduction and growth abilities. In more than 10 years of research, it has been demonstrated that *Drosophila* (Fruit Fly) eggs can be hatched successfully after freezing them in liquid nitrogen. *Drosophila* eggs frozen in this way can grow to fly and maintain their reproduction abilities. Lynch of Cornell University reported that they can reach a 75~90% hatch rate and Mazur has demonstrated that the hatch rate can reach 70~80%. Insect eggs can therefore be preserved by storing them in liquid nitrogen for an unlimited duration, as long as the egg cases are maintained at a proper permeability before being frozen and a controlled warming rate is used.

We believe that houseflies can reach high hatching rates like *Drosophila,* because they are all flies.

2. Amount of HF Eggs for Storage in Long Duration Mission

We can bring sufficient frozen HFL eggs into space because eggs are small in size, lightweight and easy to store by freezing. The eggs can maintain their reproduction and growth abilities while frozen for several decades or hundreds of years, just as human semen can live that long when frozen. According to our calculations, for every day, each astronaut needs 400 g of fresh HFL, which is equivalent to 130 g HFL powder. Powder contains about 80 g of protein (see Table 1), which meets the daily protein needs of an adult. There is a need for about 6 grams of eggs to raise 1.6 kg of HFL in 4 days and about 0.5 kg eggs for one year. Thus, for 5 astronauts in a mission of 10 years in duration, about 25 kg of eggs should be brought from earth. This is an acceptable payload to bring into space for several decades worth of food resources.

3. Storage of Food and Food Sources in Space

In this food bioregenerative system, as the food (HFL and the feeding animals) is produced daily in space locally, food storage becomes simple. It is envisioned that these food sources will usually be reproduced by themselves in space too. There are two kinds of storage, one is for the storage of animality foods (animal meat and eggs) and maggot powder. This type of storage is the same as on earth for common frozen storage. Another kind of storage involves food source storage, such as the storage of fly eggs, animal eggs, oosperm and placenta. These items can be frozen in liquid nitrogen for cryopreservation for long durations. The technology of frozen storage, and re-warming these items while maintaining their strong reproduction and fast growth abilities has been basically solved on earth. These food sources can be preserved for a long time by storing them in liquid nitrogen. Theoretically, they can be stored for an unlimited duration and can recover from thawing. There is no need for great care with these food sources during long-term freezing. They can be removed from storage and unfrozen easily at any time.

HFL Rearing and Waste Recycling in Space

The feedstuff for HFL in space is very simple, mainly using human and animal wastes (manure), inedible parts of space animal bodies and crops. HFL readily feed on fresh human waste as its feedstuff, because human waste contains rich nutrition. Most nutrients from all of these wastes can be provided back to the crew by taking the food from animals which are fed by HFL.

The residues remaining after rearing HFL are odorless and can be used by crop plants as high grade fertilizer.

1. The formulation of feedstuff for HFL (weight percent of the feedstuff), is varied on different animals:

Fresh human waste (feces and urine) and fresh animal waste (manure and animal body residues): 85~90%.

Residues of space crops (wheat bran, bean dregs, and pieces of crop stalk/leaf): 10~15%.

2. Processing of the Feedstuff Before Feeding:

Mixing of above composition in a closed container, humidity of the feedstuff in range of 70%±5% (adjusting by the volume of the urine), temperature in 25–30° C., keeping the feedstuff as fresh as possible.

3. Transplanting of the HF Egg On the Surface of the Feedstuff:

The HFL eggs are removed from their liquid nitrogen container in ultra-low-temperature frozen storage, and then warmed for hatching. For a suitable density of feeding HFL, 1 kg feedstuff may be matched with 1.0~1.5 gram HFL eggs.

4. The Conditions for Rearing:

Serial numbers may be provided on the containers used for rearing HFL. The number depends on the output needs of the HFL. The containers are all closed for odor control. In the containers: the temperature is 28±2° C., the humidity is 70±5%. Aeration pipe is installed in both the upper and middle layers for good aeration and oxygenation, and to keep the aeration speed with 1 grade. The odor flowing in the aeration pipe will be filtrated by the deodorizer. The feedstuff is stirred once a day to avoid overheating and internal oxygen shortages after placing fly eggs in the feedstuff. Before rearing, the feedstuff and containers should be placed in a microwave oven for bactericidal processing. The interior of the containers should be maintained in the dark with darkness.

5. The Structure of the Containers and the Earing Procedure:

Each container volume is 40×40×12 CM$^3$. It is much smaller than that on earth, because in microgravity, HFL and feedstuff have to closely touch in order to keep feeding all the time. Usually, 1 kg of mature FHL can be produced within one rearing cycle of 3~3.5 days for each container. The container is divided by three layers with thickness of 8 cm and 2 cm and 2 cm respectively. The upper layer is 8 cm thick for HFL rearing only. It is full of feedstuff. The middle layer with a thickness of 2 cm contains wet wheat bran or bean dregs for decontaminating the viscera of the HFL after 3 days of rearing. The lower layer with a thickness of 2 cm contains wet wood bits or silver sand for making the mature HFL, hungry, collecting and cleaning the mature HFL. There are two mesh screens between the three layers. The HFL skin can be cleaned while it goes through the tight screen opening. The HFL, can be driven to middle and lower layers by strong lighting on the surface of the layer and can stay in both of the layers for 3~4 hours respectively. They can then be collected in the lower layer after 3.5 days of rearing. Do not take 4 days as the collecting time, as this is considered to be the maximum biomass harvest for HFL to prevent any HFL from becoming pupa. After rearing HFL, all the residue, which consists of water and useful contents, can be recycled as fertilizer for space crop plants.

Rearing HF in Space.

Fly rearing and reproduction could be a standby method for sudden use in long term missions. Moreover, it is easier to rear HFL than HF in space, so a great deal of breeding space, labor and expense for rearing flies can be saved. In normal situations, there is no need to rear flies on long term missions because the problem of storage of HF eggs has been solved. But as a contingency upon losing eggs, the crew can rear houseflies to make up for the lost eggs. Therefore the technology of rearing houseflies should be reserved. Rearing HF in space shall take into consideration the following points 1. Rearing quantity and density:

The rearing density of HFL on the ground in large scale is 40000–60000/m3, but in space, where the crew only needs to rear a small number of flies for egg collection, flies can be reared in a cage with a size of 40×40×40 cm$^3$. It is a closed cage having four cage walls each of which is all mesh for aeration. For one fly, its minimum active range is 10 cm$^3$, so 3000 pairs of flies can be reared in one cage. In this cage, 13~15 gram eggs can be laid every day. (600 eggs can be laid by one pair of flies within 10 days, one gram of eggs contain 12000–14000 eggs, so 3000 couple flies can lay 13~15 gram per day). This is sufficient for the food source needs of 9~10 crew every day. (one crew need 1.5 gram fly eggs as the daily food source)

2 Feedstuff:

The feedstuff of ovipositing HF is required to be better than that of HFL, because houseflies like to eat HFL paste (smash live HFL into paste), and fortunately, the HFL paste could be easily produced self-sufficiently in space. A formula for the feedstuff for HF in space contains:70% of HFL paste and 30% of wheat bran or bean dregs.

3 Approach for Rearing FL in Space:

HFL may be reared as mentioned above. Before HFL reach maturity, they usually take 4 days of rearing.

The HFL are all in the lower layer of the rearing container with wood bits for pupating, at a temperature within 24~32° C., a humidity of 60~70%, kept in the dark with an aeration speed of 0.5~1.0 grade. Choose the pupa whose weight is more than 18 mg as the seed. Pupa will have eclosion after 5–7 days, while HF can oviposit 3 days after eclosion and the ovipositing period is 30 days or so. As a rule, HF will be killed after 15 days of ovipositing and egg gathering will be terminated to assure satisfactory egg quality.

The rearing temperature in the HF rearing cage is 28~30° C., the humidity is 60~70%. The feedstuff for rearing HFL is supplied using a small feedstuff box in the cage, including an absorbed water sponge, feedstuff sponge and lured ovipositing sponge (the sponge absorbs water and feedstuff to prevent the water and feedstuff from floating off under the microgravity). In addition to fresh human feces as ovipositing lured matter paste on, the feedstuff is the same to be applied on the lured ovipositing sponge, which can be put into 3 days after eclosion of pupa, at intervals of 12 hours. These three sponges should be alternated and the HF eggs could be collected once every morning and afternoon. The rearing cage needs to be sterilized with ultraviolet ray before rearing, HF pupa comes to eclosion after being disinfected by using potassium permanganate. Rearing HF requires lighting. Longer lighting times provide greater benefits for FL growth and ovipositing.

Processing of HFL Powder

1) Steps: Collecting Fresh HFL→Cleaning→Drying→Grinding→bactericidal procedure→Collecting powder→Package→Storage
2) Drying: Microwave under 80° C.
3) Drying within 6 hours after collecting HFL to prevent fresh HFL from becoming pupa.
4)

The HFL powder can be stored by freezing for long term preservation.

Application of HFL as Feedstuff for Animals:

Due to the rich protein and other nutrition that HFL contain, applying HFL as feedstuff provides good animal protein and other rich nutrients to poultry, livestock and aquatics to achieve large rate of reproduction and survive. This has been demonstrated by many countries in the world. As the intake ratio of hens fed by feedstuffs is about 30%, a great deal of nutrition are left in the hen's manure. HFL can recycle the nutrition from manure. Researchers have conducted experiments that demonstrate that when HFL are reared on the manure from three hens, the nutritional demand of two hens may be met. Thus, only one hen's feedstuff can sustain three hens. This is the best proven example for HFL fed by manure. The method can not only save feedstuffs, but also assure good health.

Feeding Animals on HFL in Space:

The proportionate nutrients of HFL powder are of free of pathogens and toxicity and have a quite mild taste. From its nutritive value and special health-keeping capabilities, HFL should be an ideal food for humans in space. This is the most simple food chain for recycling waste in space. But in fact, people's cultural barriers and eating habits make it rather difficult to accept insects as food (not to say HFL, the dirty insects with human waste as their food)., in the environment of space. Therefore, in our design, the first key step we must complete is to convert all wastes from human, animals and space crop efficiently into HFL. The second step is to take HFL as animal feedstuff. These animals and their eggs are looked upon as human food. In this way, the HFL and animals will be the medium loops between the human food and wastes. Their function is to recycle wastes to be human food. Thus, a closed food chain, food to waste to food can be completed with HFL and feeding animals. The embarrassment of taking HFL as the human diet can be avoided. HFL as the animal food and animals as the human food can be easily accepted. Researchers have successfully fed poultry, aquatics, amphibians, and livestock maggots both in farms and labs.

In this invention, we recommend the partridge, tilapia and America bullfrog as the first candidates for space testing animals, (the swine may be a future candidate). The reason to choose the above-mentioned three kinds of animals as the space feeding animals is that they have common grounds as follows:

Their feedstuff all can be self-sufficient in the space. The favored feedstuff of these animals is living HFL and HFL powder, and a supplemental feedstuff is inedible crops (wheat bran, bean dregs and so on). During their puerile stage, these animals can be fed with HFL power with added inedible crops and they then can be fed by adding living HFL after they grow up.

These animals are successfully fed on the earth by feeding maggot who convert the nutrients from animal waste. Researchers have demonstrated this in feeding tests using chicks, pigs, catfish and tilapia, frogs, and partridges.

Researchers Have also Demonstrated that these Animals can be Fed in the Space

For example, in February, 1999, 37 partridges were hatched from 60 partridge eggs by the crew in Russian Peace ISS. Even though there was a bad environment of strong space radiation, 10 were alive. In an embryology study of South African Frog performed on the US STS-47 Space Shuttle it was shown that eggs could be laid by frogs in space. Those eggs hatched intopolliwogs. Experiments with fish and spawn have also been performed by researchers successfully.

Another significant advantage of feeding aquatic animals is that they originally live in the water which is similar to the microgravity environment of the space. Therefore, their zoology in the space, especially taking food and reproduction in water, will be the same as on the earth and not affected by microgravity. FHL can survive for over 24 to 48 hours on the water surface, so it is convenient for the aquatic animals to eat active FHL in the water as on earth.

Water is a basic source for the survival of humans and animals in space. Fortunately, there is information indicating the apparent presence of ice in permanently shaded area at the south pole of the Moon. Also water is known to exist on the polar ice caps and below the surface of the Mars. Once these water resource can be exploited on these planets, it will be easily to rear various aquatic animals on a large scale by feeding them maggots.

The eggs of these animals can be brought from earth and be stored in liquid nitrogen for long term cryopreservation, just the same as the fly eggs, and can then be hatched after thawing. Moreover, they can reproduce by themselves in space.

These animals have small sized bodies, fast growth, rapid maturity, high rates of oviposition, can be densely reared, and are strong in anti-illness and adaptation. Their meat is all high protein food with low fat and low cholesterol, easy for digesting with good taste. In the example of partridge, its ovipositing term will be 35–45 days after hatching. The rate of oviposition is higher then 80%, weight rate of egg/body is 2.5~2.7 times higher than that of chicken. Partridges have a small appetite—the weight ratio of diet/egg is 3. Partridges like to eat maggots. The maggots like to eat partridge manure. In our 60 partridge feeding tests with HFL, the daily manure of two adult men and 60 partridges, with adding 10% manure weight of wheat bran as the feedstuff for rearing HFL from 2.5 gram of HF eggs, can harvest around 600 g fresh HFL every day. The partridge average weight increases 13% by feeding daily diet with living HFL (10 g HFL+25 g normal feedstuff) compared with a control group having a normal diet (40 g normal feedstuff) within a 27-day feeding period. This is similar for the tilapia, whose maturation term is very short and which can be used for food 2–3 months after hatching and which can oviposit and hatch by themselves at a high rate while being fed in a closed water tank without much care.

The Technologies for Rearing these Animals on Earth are Mature and Well Known.

The Safety of the HFL and HFL Powder:

(1) The Pathogen-Free Nature of HFL and HFL Powder:

HFL have special immunity abilities for resisting bacteria. Their bodies contain many kinds of active protein that resist bacteria more strongly than penicillin.

The bacteriological interactions associated with manure digestion by maggots are favorable. Maggots are competitors with bacteria for nutrients and often reduce bacterial numbers or eliminate them altogether. Maggots may consume and digest microorganisms and produce antibacterial and/or fungicidal compounds. Numerous studies using dried, rendered and fresh maggots as animal feed have revealed no health problems resulting from this practice. Culturing of self-collected soldier fly prepupae from a recent swine trail revealed no pathogens. Researchers have demonstrated that assays of 100 g HFL powder using the above-mentioned processing steps are free from colic bacillus and pathogens. The total bacteria count is lower than standard milk powder. This shows that HFL powder is edible as human food.

To rear HFL in space, the eggs are retrieved from cryopreservation; the feedstuff and rearing containers can be disinfected in advance; the processing of the HFL powder is performed using bactericidal procedures. As a result, the HFL and HFL powder can be assumed to be pathogen free.

(2) Without Poison:

Researchers have produced data analysing the ingredients of HFL powder and have demonstrated that HFL powder is a protein-rich food without any poisons.

Ideal Fertilizer for Space Crop-the Residues After Rearing HFL:

In our experiments, the wastes (35% fresh human dejection+55% partridge manure and+10% wheat bran ) were digested by HFL quickly. The odor from the waste is almost gone after one day of rearing. The residual waste is reduced 57% after 3 days of rearing.

Researchers have reported that after HFL digestion of hen manure, residues still contain 15% protein. This can be used as a soil improvement agent or fertilizer. Further, 80% of the hen manure is converted by HFL and loses about half of the moisture, dry matter and total weight at the same time, only keeping its ash the same.

Researchers have reported that after HFL digest the hen manure, the residue contains 17.62% protein, nitrogen is reduced from 7.5% to 2.6%, and phosphorus is reduced from 3.4% to 1.8%. Other researchers have reported that their manure management system (using black soldier fly) can reduce residual manure by 50%, including a 24% reduction in nitrogen concentration within this 50% residual manure, resulting in total nitrogen reduction of 62%. More recently, researchers have suggested that a higher rate of nitrogen removal is possible, as is a significant reduction in phosphorus. It is evident that nitrogen and phosphorous removal from wastes by their incorporation into maggot biomass will provide a significant benefit in nutrient management.

Researchers have reported that the manure residues remaining after HFL digestion are a kind of humic matter with no infective pathogens. Use of these residues as fertilizer for tomato, cucumber, black mushrooms etc. can produce high rates of production and good quality. Researchers have reported that using HFL, one can convert 100 Kg of fresh hen manure or cow manure to 2~3 kg of protein feedstuff and can produce 50~60 kg of dry and odorless soil improving agent. As maggots can reduce pathogens in human/animal waste, they may make it safer for organic vegetable production.

Other Functions of Maggot Powder:

Due to lack of protection from the earth's atmosphere and magnetic field in space, there are harmful effects on the human body due to strong space radiation when humans live in space. These effects include a reduction in the number of white blood cells and immune cells, cancer, damage to fertility, etc. The desire to resist the harmful effects of space radiation has lead to research programs at NASA and in many countries of the world, but to date no effective way to overcome these effects has been developed.

Tests have proved that eating maggot powder as a healthy food, can improve the ability of animals and humans to resists harmful radiation and immune function effects. For patients under treatment using radiation or chemical therapies, the reduction of white cells and immune cells obviously slows down and hair lost is apparently decreased. The ingredient in maggot bodies that provides these functions is not certain, but there is a significant clinical effect for humans living in space or on earth. Crops or animal internal organs could serve as feedstuff for rearing maggots on earth or in space, some herbal medicines and other ingredients with special function can be added in those feedstuff, or into maggot (pupa) powder for increased effect. These can also be taken by the people who are exposed to radiation or live in locations that are polluted by radiation. Furthermore, animals that feed on maggots, their meat and eggs can experience similar benefits. The daily dose for adults is 0.3~1.0 gram of pure maggot (pupa) powder.

Maggots can also be used as carriers for special ingredients by feeding the maggots with relevant ingredients that humans need, such as vitamins, minerals, electrolytes and antibiotic etc. With this approach, the animals reared on the maggots will serve as carriers for the relevant ingredients by virtue of being fed on the maggots.

Researchers have exploited maggot carriers, for example, it has been demonstrated that maggots can contain enough antibiotics and trace elements by rearing maggot with relevant ingredient.

Merits of Rearing Maggots On Long Term Missions

The full recycling of the wastes of human/animals and inedible crops in space is possible by rearing maggots which will be nourishing feedstuff for feeding animals, the animals and crops will be human food. This provides a regenerative closed-loop food system in space.

2. Maggots are an ideal food source that offers many types of nutrition such as rich protein, fatty acid, amino acids, vitamins, minerals, electrolytes and many unknown nutrients. Combined with the animals fed by maggots and crops, they can meet most nutritional needs for humans on long-term space missions.
3. Frozen fly eggs and animal eggs, oosperm and placenta, can be frozen in liquid nitrogen for cryopreservation to provide a safe and sufficient food source and food ingredient storage arrangement for long term missions.
4. Maggots and feeding animals all have strong reproduction abilities, short life cycles and high growth speeds. Maggots are easy to rear continuously day and night at high densities to achieve efficient and self-sufficient food production.
5. Maggots seldom get diseases. Rearing maggots and processing maggot powder are pathogen-free and chemical-free activities. Using maggots to feed animals for human foods is safe, and does not produce harmful substances which could pollute the environment.
6. Technologies for rearing maggots and animals are well developed and can be easily transferred to space applications with minimal research investment and time. To rear maggots one only needs simple production equipment, operation, and techniques. The food production, processing and storage activities are all performed with little space, so that the cost of food production, processing, storage and waste recycling can be minimized.

What is claimed is:

1. A method for closed-loop regeneration of food for humans during a long term mission in space, comprising:
   freezing fly eggs in liquid nitrogen;
   bringing the frozen fly eggs on the long term mission;
   thawing some of the fly eggs in space;
   rearing maggots and pupa in space from the thawed fly eggs by feeding the maggots human waste and plant crop waste;
   preparing a powder from the maggots that have been reared; and
   feeding the maggot powder to the humans as food.
2. The method defined in claim 1, further comprising using the maggots as a carrier by feeding the maggots with vitamins, minerals, electrolytes and antibiotics that the humans need.
3. The method defined in claim 1, further comprising:
   using the maggots, the pupa, and the maggot powder as feedstuff for poultry, aquatic animals, amphibians, and livestock; and
   using the poultry, aquatic animals, amphibians, livestock and their eggs as nourishing food for the humans in space.
4. The method defined in claim 1, further comprising:
   raising animals by feeding the animals the maggots and pupa while alive and by feeding the animals the maggot powder; and
   using the animals and the maggot powder as healthy food for the humans to assist in resisting radiation and improving immune abilities.

* * * * *